United States Patent
Komiya et al.

(10) Patent No.: US 12,362,088 B2
(45) Date of Patent: Jul. 15, 2025

(54) SCANNING COIL, SCANNING MAGNET, AND METHOD FOR MANUFACTURING SCANNING COIL

(71) Applicants: KABUSHIKI KAISHA TOSHIBA, Tokyo (JP); TOSHIBA ENERGY SYSTEMS & SOLUTIONS CORPORATION, Kawasaki (JP)

(72) Inventors: Gen Komiya, Kokubunji (JP); Toshiyuki Nakano, Yokohama (JP); Tomofumi Orikasa, Yokohama (JP); Toshiro Fujii, Yokohama (JP); Hiroko Onoda, Kawasaki (JP)

(73) Assignees: KABUSHIKI KAISHA TOSHIBA, Tokyo (JP); TOSHIBA ENERGY SYSTEMS & SOLUTIONS CORPORATION, Kawasaki (JP)

( * ) Notice: Subject to any disclaimer, the term of this patent is extended or adjusted under 35 U.S.C. 154(b) by 429 days.

(21) Appl. No.: 17/580,722

(22) Filed: Jan. 21, 2022

(65) Prior Publication Data
US 2022/0148790 A1    May 12, 2022

Related U.S. Application Data

(63) Continuation of application No. PCT/JP2020/046171, filed on Dec. 10, 2020.

(30) Foreign Application Priority Data

Dec. 13, 2019 (JP) .................................. 2019-225104

(51) Int. Cl.
*H01F 27/32*  (2006.01)
*H01F 27/28*  (2006.01)
*H01F 41/04*  (2006.01)

(52) U.S. Cl.
CPC ....... *H01F 27/2823* (2013.01); *H01F 27/325* (2013.01); *H01F 41/04* (2013.01)

(58) Field of Classification Search
CPC ..................................................... H01F 27/325
(Continued)

(56) References Cited

U.S. PATENT DOCUMENTS 3,430,169 A * 2/1969 Gabor .................... H01J 29/762
                                                                335/213
3,757,224 A * 9/1973 Fedorko ................. H01J 29/764
                                                                335/213
(Continued)

FOREIGN PATENT DOCUMENTS

JP      2006-135060 A    5/2006
JP      2008-270242 A    11/2008
(Continued)

OTHER PUBLICATIONS

International Search Report issued Feb. 16, 2021 in PCT/JP2020/046171 filed on Dec. 10, 2020, 2 pages.

*Primary Examiner* — Alexander Talpalatski
(74) *Attorney, Agent, or Firm* — Oblon, McClelland, Maier & Neustadt, L.L.P.

(57) ABSTRACT

According to an embodiment, a scanning coil includes a bobbin, a conducting wire, and a resin for fixing the conducting wire. The bobbin includes a main body having a truncated conical cylindrical outer shape in an integrated or assembled state and made of an electrically insulating material, a wire-laying path which is formed in the main body and in which a conducting wire is installed, and a plurality of holding parts formed along the wire-laying path on an inner peripheral surface side of the main body and with axial intervals therebetween.

6 Claims, 13 Drawing Sheets

(58) Field of Classification Search
USPC .................................................. 335/210, 213
See application file for complete search history.

(56) References Cited

U.S. PATENT DOCUMENTS

| | | | | | |
|---|---|---|---|---|---|
| 4,117,432 | A | * | 9/1978 | Shizu | ...................... H01J 29/76 335/213 |
| 4,243,965 | A | * | 1/1981 | Yoshikawa | ........... H01J 29/764 335/213 |
| 4,338,584 | A | * | 7/1982 | Howard | ................ H01J 29/826 335/212 |
| 4,464,643 | A | * | 8/1984 | Meershoek | ........... H01J 29/762 313/428 |
| 4,484,166 | A | * | 11/1984 | Osinga | .................... H01J 29/76 313/431 |
| 4,682,134 | A | * | 7/1987 | Laskaris | ................... H01F 6/00 505/879 |
| 5,111,173 | A | * | 5/1992 | Matsuda | .................. H05H 7/04 335/216 |
| 5,446,432 | A | * | 8/1995 | Ikeuchi | ................... H01J 9/236 313/433 |
| 5,828,278 | A | * | 10/1998 | Murata | ................ H01J 29/762 348/828 |
| 6,344,781 | B1 | * | 2/2002 | Slenker | ................... H01F 17/04 361/768 |

FOREIGN PATENT DOCUMENTS

| | | |
|---|---|---|
| JP | 2020-010824 A | 1/2020 |
| JP | 2020-041971 A | 3/2020 |
| WO | WO 2015/090776 A1 | 6/2015 |

* cited by examiner

SCANNING COIL, SCANNING MAGNET, AND METHOD FOR MANUFACTURING SCANNING COIL

CROSS-REFERENCE TO RELATED APPLICATIONS

This application is a continuation application of International Application PCT/JP2020/046171 filed on Dec. 10, 2020, the entire content of which is incorporated herein by reference. This application is based upon and claims the benefit of priority from Japanese Paten Application No. 2019-225104, filed on Dec. 13, 2019; the entire content of which is incorporated herein by reference.

FIELD

Embodiments of the present invention relate to a scanning coil, a scanning magnet using the same, and a method for manufacturing a scanning coil.

BACKGROUND

In a heavy particle beam therapy facility, a therapy of killing a cancer tissue is performed by thoroughly irradiating the spot of a patient with a beam accelerated up to a high energy level. For example, in order to irradiate with a narrowed carbon beam for irradiation as it is, high-level control needs to be performed. To this end, scanning magnets are placed in horizontal and vertical directions with respect to a beam line. To form a high level magnetic field by a scanning coil constituting the scanning magnets, a large current needs to be conducted to the scanning coil. Further, to highly control the beam, the conductor in the coil is required to be accurately placed according to the design.

From the above background, there is a proposed method of applying an adhesive composed of a phenoxy resin in advance to the surface of a bobbin, placing a superconducting wire while fusing it, and then fixing the outer periphery of the superconducting wire with an epoxy resin containing a filler. The use of a superconducting state can provide a compact coil realizing a high magnetic field.

The method for manufacturing the above scanning coil has the following problem.

In the scanning magnet, a large current needs to be conducted to the conducting wire to form a magnetic field. By using the superconducting state as in the above example, a high magnetic field can be achieved by the compact coil. However, in order to excite the scanning coil into the superconducting state, an expensive superconducting wire and a special freezer are required. On the other hand, in the case of the scanning coil by a normal conducting wire, there is such a problem that the wire diameter becomes large resulting in increasing the stiffness and causing a difficulty in accurately placing the conducting wire in the conventional manufacturing method.

DETAILED DESCRIPTION

Figure 1:
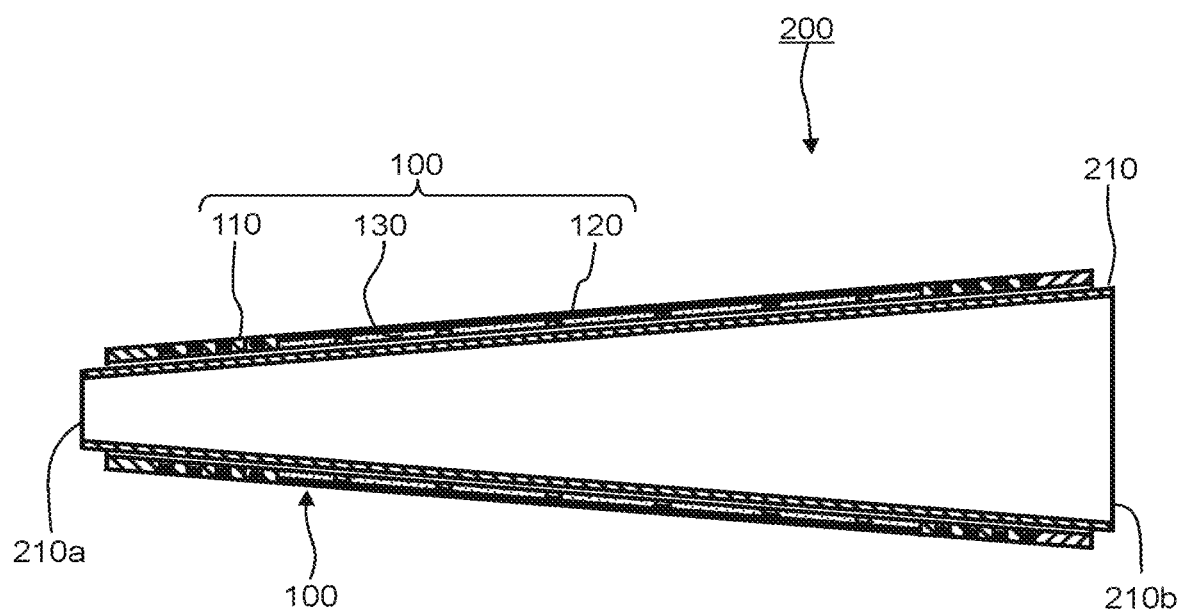
FIG. 1 is a longitudinal sectional view illustrating a scanning magnet according to a first embodiment.

An object of embodiments of the present invention is to enable highly accurate placement of a conducting wire of a scanning coil.

According to an embodiment, there is provided a scanning coil comprising: a bobbin including a main body having a truncated conical cylindrical outer shape in an integrated or assembled state and made of an electrically insulating material, a wire-laying path formed in the main body, and a plurality of holding parts formed along the wire-laying path on an inner peripheral surface side of the main body and with axial intervals therebetween; a conducting wire installed in the wire-laying path; and a resin for fixing the conducting wire.

According to another embodiment, there is provided a method for manufacturing a scanning coil, comprising: a bobbin production step of producing a bobbin formed with a wire-laying path for installing a conducting wire therein; a conducting wire installation step of installing the conducting wire in the wire-laying path; a resin injection step of constructing a resin injecting assembly, injecting a resin into the wire-laying path, and curing the resin; and a mold release step of releasing the scanning coil from a mold, wherein the bobbin includes a main body having a truncated conical cylindrical outer shape in an integrated or assembled state and made of an electrically insulating material, the wire-laying path formed in the main body, and a plurality of holding parts formed along the wire-laying path on an inner peripheral surface side of the main body and with axial intervals therebetween.

Hereinafter, a scanning coil, a scanning magnet, and a method for manufacturing a scanning coil according to embodiments of the present invention will be explained referring to the drawings. Throughout the drawings, same or similar sections are denoted by the same reference symbols and will not be described repeatedly.

First Embodiment

FIG. 1 is a longitudinal sectional view illustrating a scanning magnet according to a first embodiment, namely, a sectional view along a longitudinal direction.

A scanning magnet 200 has a beam duct 210 and two scanning coils 100.

The beam duct 210 is a duct that forms a space where a beam flies toward an irradiation object. The beam duct spreads from a small-diameter part 210a toward a large-diameter part 210b in a flight direction of the beam at a portion of the scanning magnet 200, so as to scan the beam on the irradiation object, and thereby has a shape capable of covering the change in angle of the beam.

The two scanning coils 100 are formed integrally with each other in a manner to sandwich the beam duct 210 therebetween from the outside in a radial direction, and configured to be able to change the direction of the beam. Note that the ones illustrated in FIG. 1 are coils that change the orientation of the beam in a vertical direction (an up and down direction in FIG. 1). Generally, scanning coils that change the orientation of the beam in a horizontal direction (a front and back direction in FIG. 1) are provided on the outside in the radial direction so as to enable two-dimensional scanning of the irradiation object. In FIG. 1, the illustration of the scanning coils in the horizontal direction is omitted. Hereinafter, the scanning coils in the vertical direction will be explained, and the explanation also applies to the scanning coils in the horizontal direction.

The scanning coil 100 has a bobbin 110, a conducting wire 120, and a resin part 130. Their details will be explained later. Each of the scanning coils 100 is individually manufactured, and two scanning coils 100 are finally assembled in one unit. Hereinafter, the configuration and manufacturing method of one scanning coil 100 will be explained in sequence.

Figure 2:
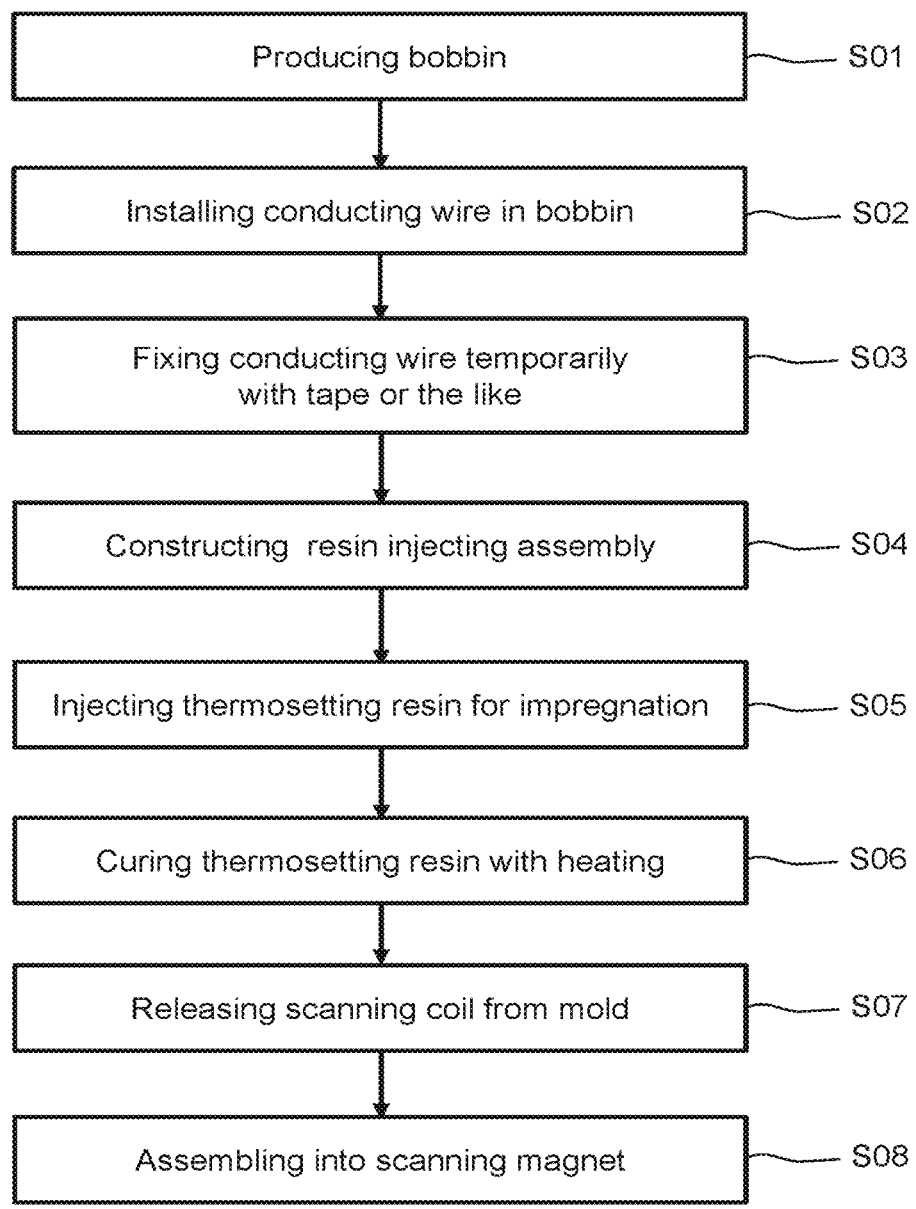
FIG. 2 is a flowchart illustrating a procedure of a method for manufacturing the scanning coil according to the first embodiment.

FIG. 2 is a flowchart illustrating the procedure of the method for manufacturing the scanning coil according to the first embodiment.

First, production of the bobbin is performed (Step S01).

Figure 3:
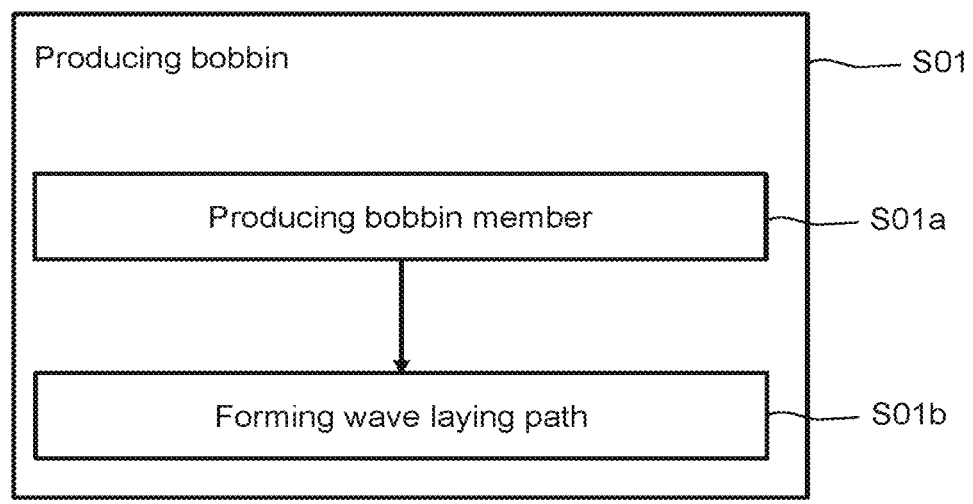
FIG. 3 is a flowchart illustrating a detailed procedure of producing a bobbin in the method for manufacturing the scanning coil according to the first embodiment.

FIG. 3 is a flowchart illustrating a detailed procedure of producing a bobbin in the method for manufacturing the scanning coil according to the first embodiment.

As for the production of the bobbin, the production of a bobbin member 110a (FIG. 4, FIG. 5) is performed first (Step S01a).

Figure 4:
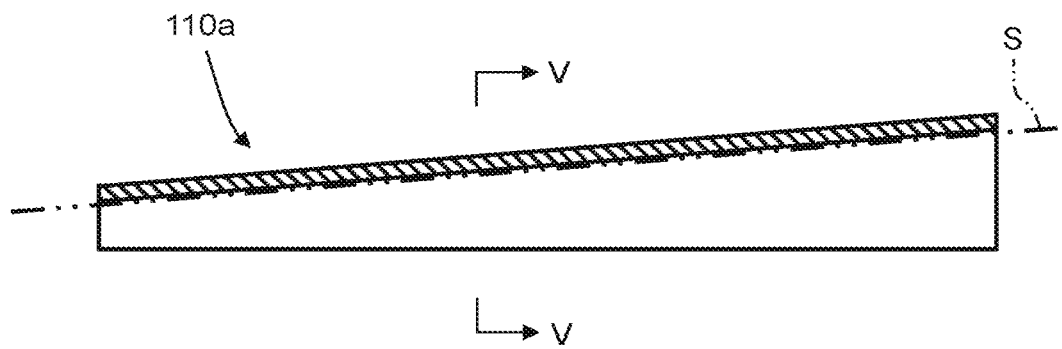
FIG. 4 is an arrow sectional view taken along a line IV-IV in FIG. 5, illustrating a configuration of a bobbin member produced in the method for manufacturing the scanning coil according to the first embodiment.
Figure 5:
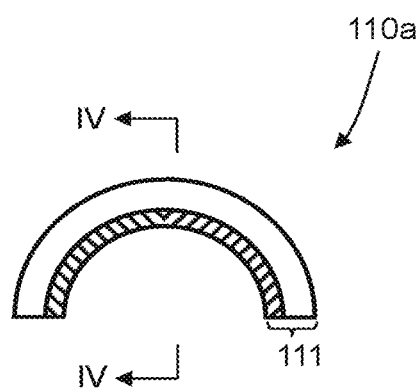
FIG. 5 is an arrow sectional view taken along a line V-V in FIG. 4, illustrating the configuration of the bobbin member produced in the method for manufacturing the scanning coil according to the first embodiment.

FIG. 4 is an arrow sectional view taken along a line IV-IV in FIG. 5, illustrating the configuration of the bobbin member 110a produced in the method for manufacturing the scanning coil according to the first embodiment, and FIG. 5 is an arrow sectional view taken along a line V-V in FIG. 4.

The bobbin member 110a is made of, for example, an electrically insulating material such as fiber reinforced plastics (FRP), and is generally formed by an injection mold. The bobbin member 110a has a main body 111 having a semicircular cross section and formed with a taper in the longitudinal direction, namely, having a cross section continuously spreading in the longitudinal direction.

In other words, the main body 111 has a shape rotated 180 degrees around a center axis C extending in the longitudinal direction. Therefore, two bobbin members 110a are integrated in a state where they face each other, and thereby form a shape of a rotation body made by 360-degree rotation. Accordingly, in the following explanation, the 360-degree rotation body (hereinafter, referred to as a rotation body) is explained in some cases. The bobbin member 110a in this embodiment is made by equally dividing the rotation body into two parts in a circumferential direction. In other words, the bobbin member 110a is the one made by dividing the rotation body by a plane including the center axis C.

The two main bodies 111 of the bobbin members 110a, in an integrated state, have a truncated conical cylindrical outer shape. In other words, the main bodies 111 linearly spread from small-diameter side end parts 111a toward large-diameter side end parts 111b in the longitudinal direction so that their inner surfaces are formed to be in contact with a virtual curved surface S of the truncated conical shape.

As for the production of the bobbin, the forming process of a wire-laying path 113 (FIG. 6 to FIG. 8) is performed next (Step S01b). Specifically, the wire-laying path 113, namely, a path for laying the conducting wire 120 (FIG. 10) is formed in the main body 111.

Note that from the viewpoint of heat dissipation, the occupancy rate of the conducting wire 120 to the cross-sectional area of the wire-laying path 113 is preferably 50 to 95%. This is because if the occupancy rate is less than 50%, the placement accuracy of a magnetic field degrades, whereas if the occupancy rate is more than 95%, the placement shape of the conducting wire 120 is distorted to similarly degrade the placement accuracy of the magnetic field.

Figure 6:
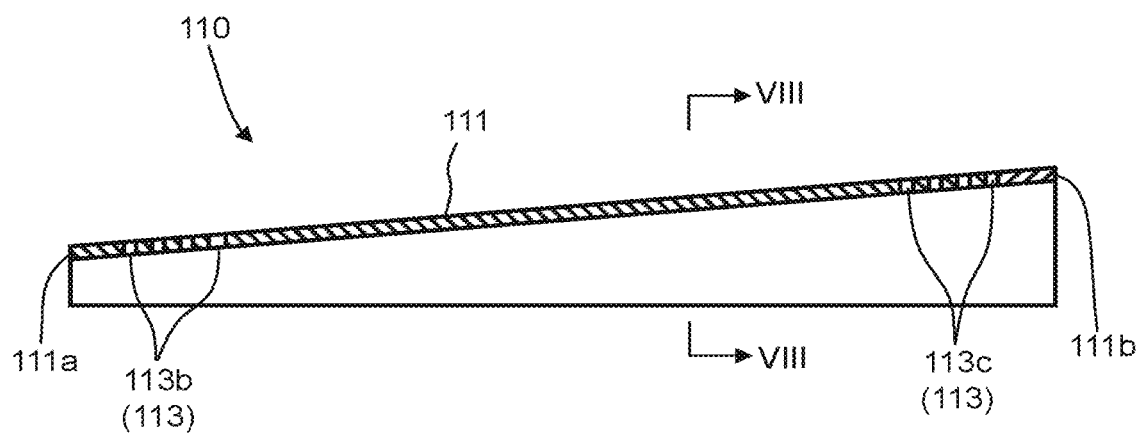
FIG. 6 is an arrow sectional view taken along a line VI-VI in FIG. 8, illustrating the configuration of the bobbin produced in the method for manufacturing the scanning coil according to the first embodiment.
Figure 7:
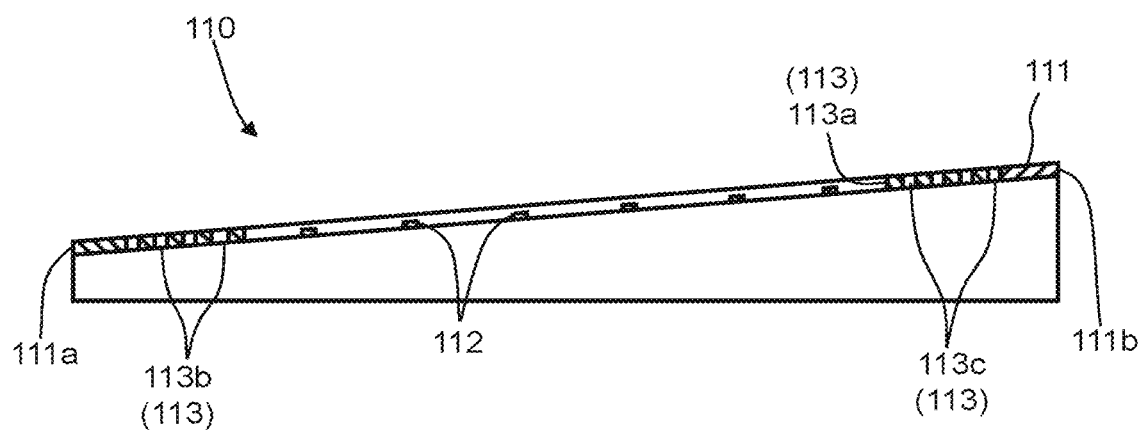
FIG. 7 is an arrow sectional view taken along a line VII-VII in FIG. 8, illustrating the configuration of the bobbin produced in the method for manufacturing the scanning coil according to the first embodiment.
Figure 8:
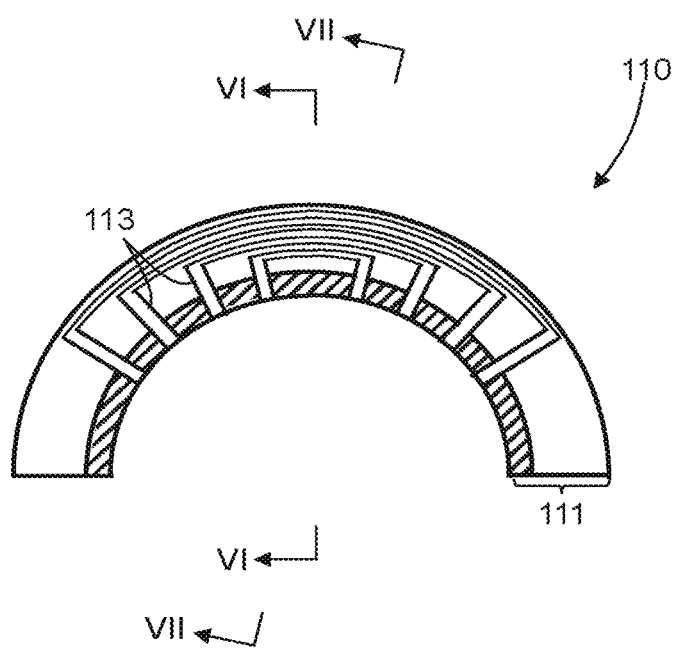
FIG. 8 is an arrow sectional view taken along a line VIII-VIII in FIG. 6, illustrating the configuration of the bobbin produced in the method for manufacturing the scanning coil according to the first embodiment.
Figure 9:
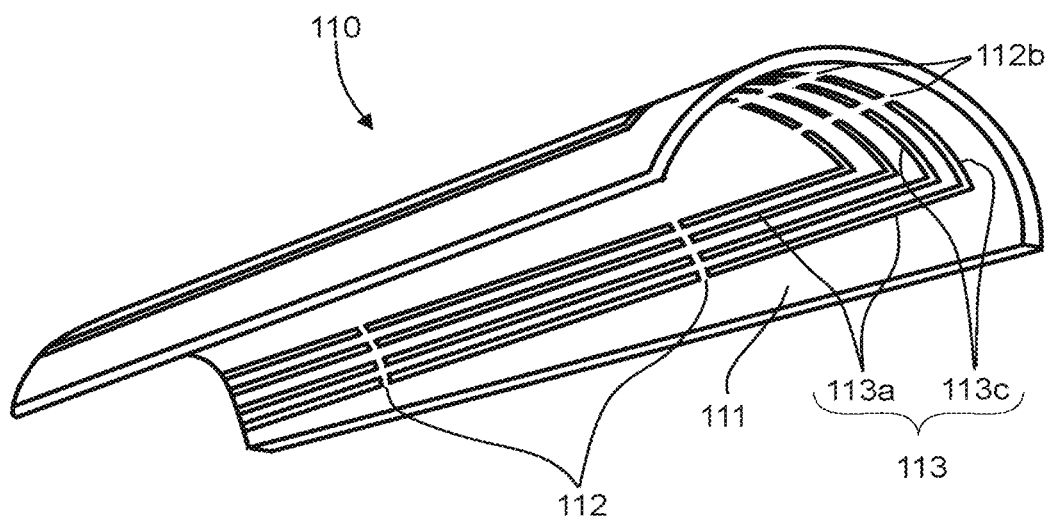
FIG. 9 is a perspective view illustrating the vicinity of an end portion on a large-diameter side of the bobbin produced in the method for manufacturing the scanning coil according to the first embodiment.

FIG. 6 is an arrow sectional view taken along a line VI-VI in FIG. 8, illustrating the configuration of the bobbin produced in the method for manufacturing the scanning coil according to the first embodiment, FIG. 7 is an arrow sectional view taken along a line VII-VII in FIG. 8, and FIG. 8 is an arrow sectional view taken along a line VIII-VIII in FIG. 6. Further, FIG. 9 is a perspective view illustrating the vicinity of an end portion on the large-diameter side of the bobbin. FIG. 6 to FIG. 9 illustrate the state of the bobbin 110 after the wire-laying path 113 is formed in the main body 111.

As illustrated in FIG. 6 to FIG. 8, the wire-laying path 113 has a plurality of long-side parts 113*a* formed in the longitudinal direction, a plurality of small-diameter parts 113*b*, and a plurality of large-diameter parts 113*c*. Note that in FIG. 8 and FIG. 9, a case having eight long-side parts 113*a*, four small-diameter parts 113*b*, and four large-diameter parts 113*c* is illustrated as an example, and the numbers of them are merely examples and decided depending on the number of turns of the scanning coil 100.

Each of the long-side parts 113*a*, the small-diameter parts 113*b*, and the large-diameter parts 113*c* of the wire-laying path 113 formed in the main body 111 reaches the inside surface from the outside surface of the main body 111. More specifically, the main body 111 is cut by the wire-laying path 113, but its whole shape is maintained by holding parts 112 provided on the inside surface of the main body 111 with axial direction intervals therebetween, and long-side holding parts 112*a*, 112*b*.

Figure 10:
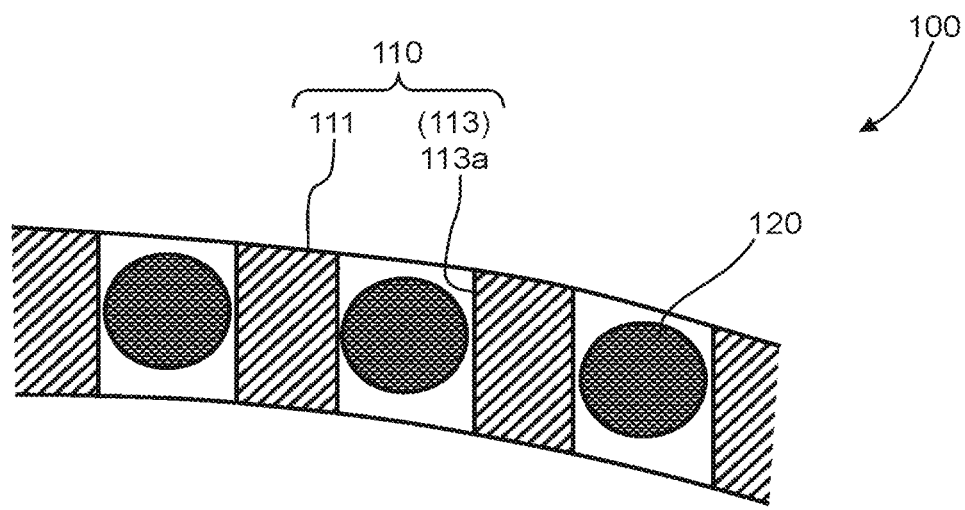
FIG. 10 is a first partial cross-sectional view illustrating the state of the installation of a conducting wire 120 in the bobbin in the method for manufacturing the scanning coil according to the first embodiment.

As illustrated in FIG. 8 and FIG. 9, the plurality of long-side parts 113*a* individually extend in the longitudinal direction with circumferential intervals therebetween to connect the small-diameter parts 113*b* and the large-diameter parts 113*c*. Though not illustrated in FIG. 9, each of connection portions between the long-side parts 113*a* and the small-diameter parts 113*b* and connection portions between the long-side parts 113*a* and the large-diameter parts 113 is formed in a shape having a radius equal to or larger than a curvature radius required to lay the conducting wire 120 therein (FIG. 10).

The plurality of long-side parts 113*a* may be formed in parallel to one another. Alternatively, each of them may be formed along an intersection line between a virtual plane including the center axis C and the main body 111.

The wire-laying path 113 is formed as one continuous path so as to be able to form a coil by installing the conducting wire 120 along the wire-laying path 113. Note that though not illustrated, the start point or the end point of the installation of the conducting wire 120 is on the inside of the small-diameter part 113*b* or on the inside of the large-diameter part 113*c*.

The wire-laying path 113 penetrates the main body 111 from the outside to the inside thereof and extends. However, as illustrated in FIG. 7 and FIG. 9, the holding parts 112 are formed with longitudinal intervals therebetween. The holding parts 112 are portions where the wire-laying path 113 does not penetrate from the outside to the inside of the main body 111. The formation of the holding parts 112 makes it possible to maintain the relative positional relation between the portions, cut by the wire-laying path 113, of the main body 111. Note that, in addition to the holding parts 112, the long-side holding parts 112*b* are provided on the large-diameter side end part 111*b* side as illustrated in FIG. 9 as portions having a holding function. Further, though not illustrated, similar holding portions are formed at the small-diameter side end part 111*a*.

Next, the conducting wire 120 is installed in the bobbin 110 produced at Step S01 (Step S02). Here, the conducting wire 120 is preferably a stranded wire for facilitating the impregnating ability of a resin.

Figure 11:
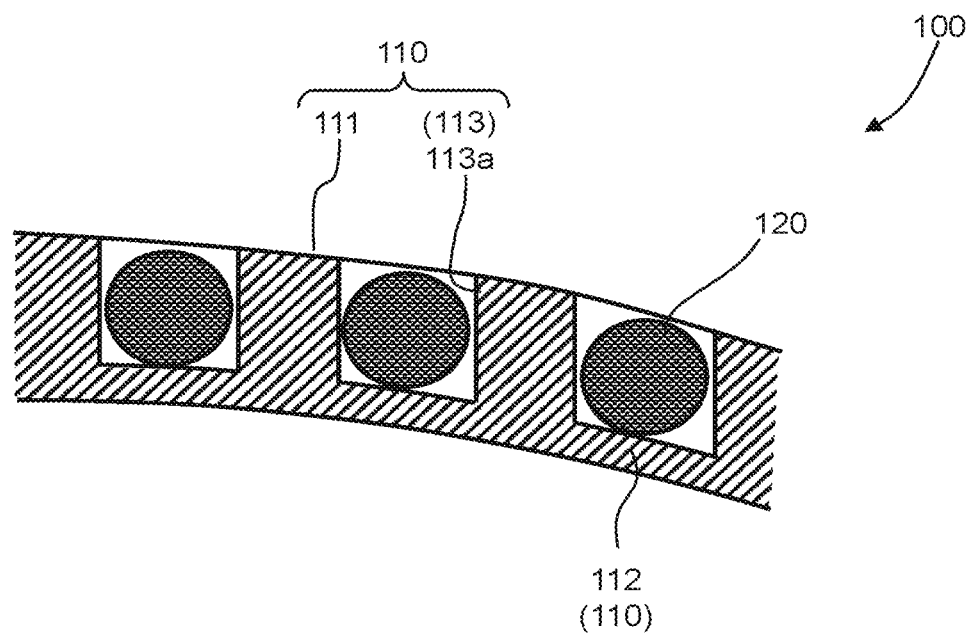
FIG. 11 is a second partial cross-sectional view illustrating the state of the installation of the conducting wire 120 in the bobbin in the method for manufacturing the scanning coil according to the first embodiment.

FIG. 10 is a first cross-sectional view illustrating the state of the installation of the conducting wire 120 in the bobbin in the method for manufacturing the scanning coil according to the first embodiment, and FIG. 11 is a second cross-sectional view. FIG. 10 illustrates a state where the conducting wire 120 is installed at a portion where the holding part 112 is not formed at the long-side part 113*a* of the wire-laying path 113. Besides, FIG. 11 illustrates a state where the conducting wire 120 is installed at a portion where the holding part 112 is formed at the long-side part 113*a* of the wire-laying path 113.

The conducting wire 120 is installed in a manner to be pressed into the wire-laying path 113 of the bobbin 110. The wire-laying path 113 is open to the interior side of the main body 111, and the holding parts 112 are arranged with intervals therebetween and the conducting wire 120 has a certain level of stiffness, so that the conducting wire 120 never projects to the interior side of the main body 111. Accordingly, the conducting wire 120 can be installed in a stable state inside the wire-laying path 113 along the wire-laying path 113.

Next, the conducting wire 120 is temporarily fixed with tape or the like (Step S03). The conducting wire 120 is large in length and the scanning coil 100 is a saddle-shaped coil, so that they do not exist within the same plane but are three-dimensionally placed. Therefore, the conducting wire 120 is temporarily fixed with, for example, tape or the like such as peel ply to prevent the placement of the conducting wire 120 from being disordered due to the subsequent resin injection or the like.

In this event, providing holes having a diameter of about 0.5 mm to 10 mm through which the resin can pass in advance at a part of the peel ply or the like enables ensuring the permeation of the resin at the injection in a later process, resulting in more reliable fixation of the conducting wire. Note that if the hole diameter is less than 0.5 mm, clogging occurs to disturb the passage of the resin, whereas if the hole diameter is more than 10 mm, the conducting wire cannot be fixed, so that the hole diameter is preferably about 0.5 mm to 10 mm.

Next, a resin injecting assembly 10 (FIG. 17) is constructed (Step S04).

Figure 12:
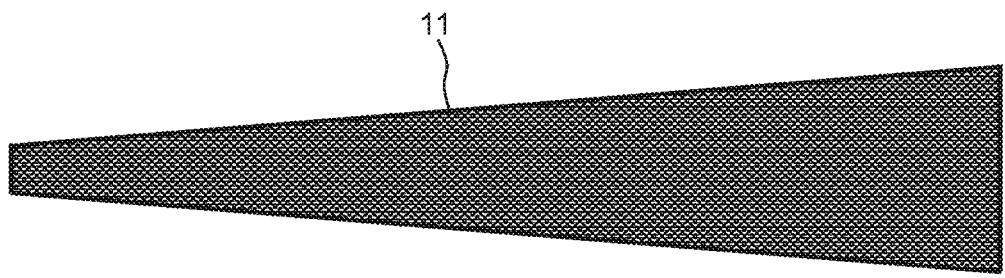
FIG. 12 is a longitudinal sectional view illustrating a core constituting a resin injecting apparatus in the method for manufacturing the scanning coil according to the first embodiment.
Figure 13:
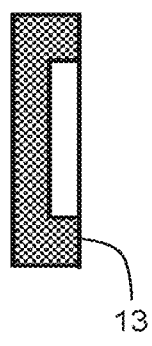
FIG. 13 is a longitudinal sectional view illustrating a small-diameter side end part closing member constituting the resin injecting apparatus in the method for manufacturing the scanning coil according to the first embodiment.
Figure 14:
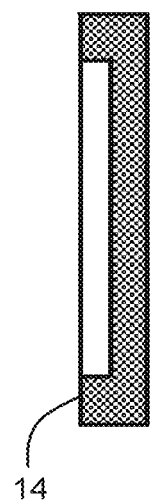
FIG. 14 is a longitudinal sectional view illustrating a large-diameter side end part closing member constituting the resin injecting apparatus in the method for manufacturing the scanning coil according to the first embodiment.
Figure 15:
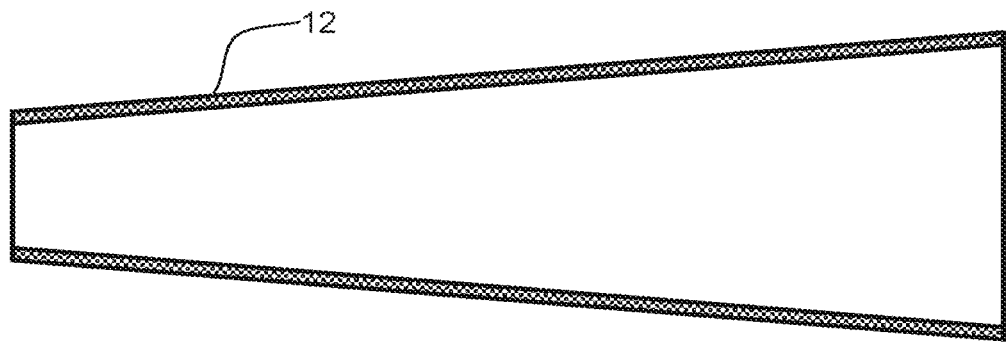
FIG. 15 is a longitudinal sectional view illustrating an outer cylinder constituting the resin injecting apparatus in the method for manufacturing the scanning coil according to the first embodiment.
Figure 16:
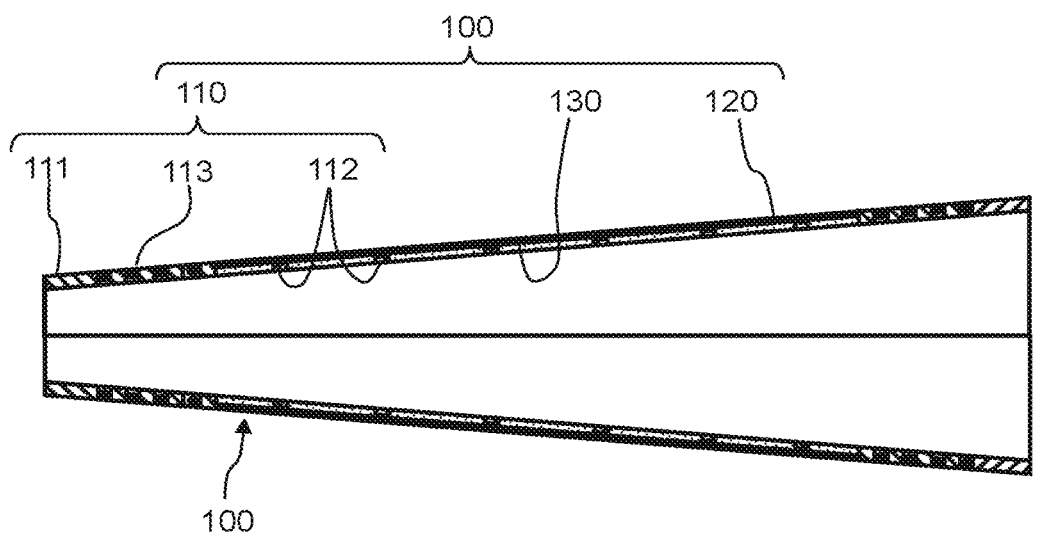
FIG. 16 is a longitudinal sectional view illustrating a state of the bobbins to which the conducting wire has been installed at the resin injection in the method for manufacturing the scanning coil according to the first embodiment.

FIG. 12 is a longitudinal sectional view illustrating a core 11 constituting a resin injecting apparatus in the method for manufacturing the scanning coil according to the first embodiment, FIG. 13 is a longitudinal sectional view illustrating a small-diameter side end part closing member 13, FIG. 14 is a longitudinal sectional view illustrating a large-diameter side end part closing member 14, and FIG. 15 is a longitudinal sectional view illustrating an outer cylinder 12. Further, FIG. 16 is a longitudinal sectional view illustrating a state of the two bobbins 110 to which the conducting wire 120 has been installed at the resin injection. Note that the illustration of the conducting wire 120 is omitted in FIG. 16.

An outer surface of the core 11 has a truncated conical shape corresponding to the inner surface of the bobbin 110 illustrated in FIG. 4. An inner surface of the outer cylinder 12 is formed to correspond to the shape of the outside surfaces of the two bobbins 110 in the state illustrates in FIG. 16 and to be in contact with the outside surfaces of the two bobbins 110. The small-diameter side end part closing member 13 and the large-diameter side end part closing member 14 are formed to fit the small-diameter side and the large-diameter side of the outer cylinder 12, respectively. Note that male screws may be formed on the inside surface of the outer cylinder 12 at the portions and female screws may be formed in the outside surfaces of the small-diameter side end part closing member 13 and the large-diameter side end part closing member 14 so as to be screwed together.

Figure 17:
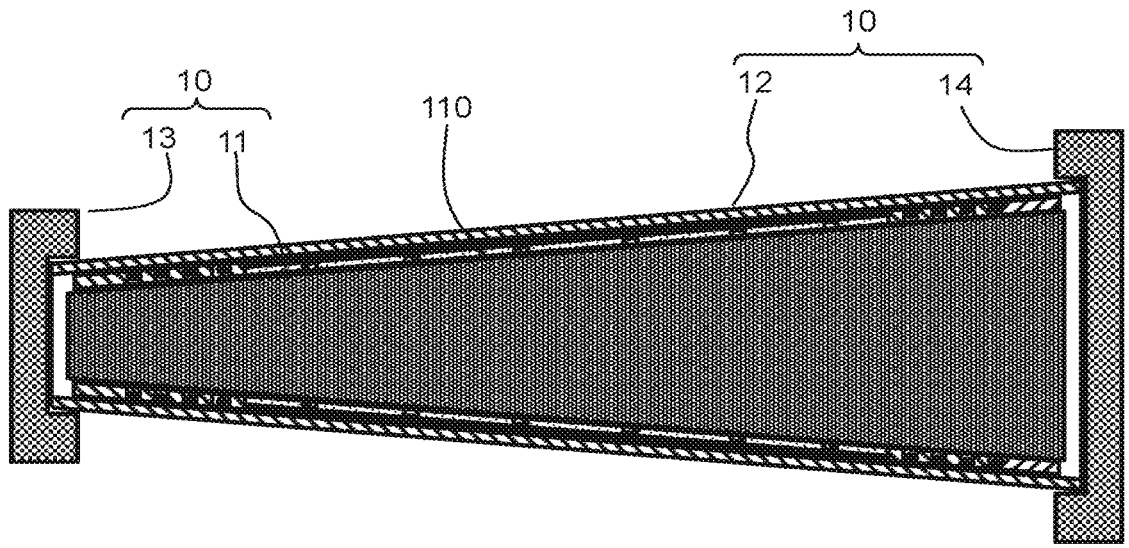
FIG. 17 is a longitudinal sectional view illustrating a state of a resin injecting assembly at the resin injection in the method for manufacturing the scanning coil according to the first embodiment.

FIG. 17 is a longitudinal sectional view illustrating a state at the resin injection in the method for manufacturing the scanning coil according to the first embodiment.

The above components are integrally assembled to constitute the resin injecting assembly 10 as illustrated in FIG. 17. Note that though not illustrated in FIG. 17, an injection port for resin injection is formed at a portion of any of the outer cylinder 12, the small-diameter side end part closing member 13, and the large-diameter side end part closing member 14. Further, an exhaust port for exhaust is formed at a portion of any of the outer cylinder 12, the small-diameter side end part closing member 13, and the large-diameter side end part closing member 14. The exhaust port may be connected to a vacuum pump for evacuation.

Next, a thermosetting resin is injected for impregnation (Step S05). The method in this event may be a method of injecting the resin from the injection port and exhausting inside air from the exhaust port, or a method of first performing evacuation from the exhaust port and then injecting the resin from the injection port.

When an anhydride-curing epoxy resin is used as the thermosetting resin, the impregnation to between the bobbin 110 and the conducting wire 120 becomes better because of effectiveness in terms of time and viscosity until the resin is gelated. Further, by filling with molten silica, crystalline silica, alumina, magnesium oxide at a volume filling ratio of 30 vol % or more, the heat conductivity of the epoxy resin rises to enable efficient dissipation of heat generated in an electrical conductor by energization to the scanning coil 100.

Next, the thermosetting resin is cured with heating (Step S06).

After the resin is cured, the scanning coil 100 is released from the mold (Step S07). In this event, the tape or the like used for temporary fixation at Step S03 is also removed.

Figure 18:
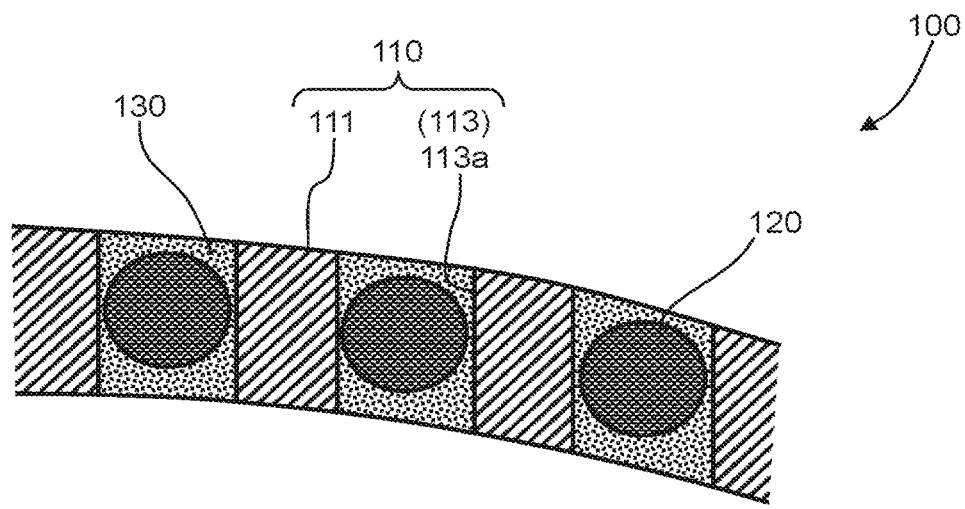
FIG. 18 is a first partial cross-sectional view illustrating a state after the resin injection in the method for manufacturing the scanning coil according to the first embodiment.
Figure 19:
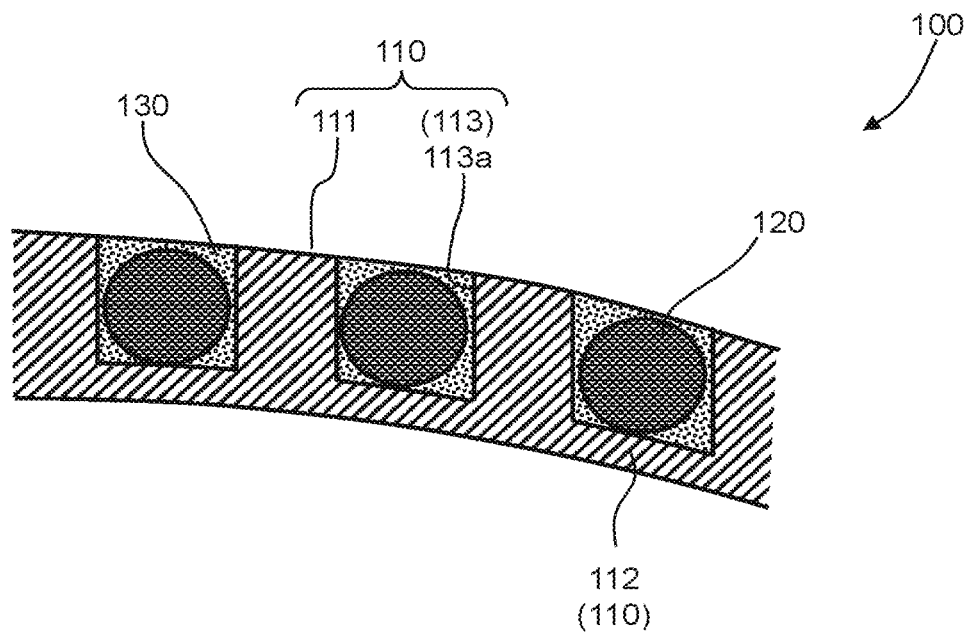
FIG. 19 is a second partial cross-sectional view illustrating the state after the resin injection in the method for manufacturing the scanning coil according to the first embodiment.

FIG. 18 is a first partial cross-sectional view illustrating a state after the resin injection in the method for manufacturing the scanning coil according to the first embodiment, and FIG. 19 is a second cross-sectional view. FIG. 18 illustrates a portion where the holding part 112 is not formed at the long-side part 113a of the wire-laying path 113, and FIG. 19 illustrates a portion where the holding part 112 is formed at the long-side part 113a of the wire-laying path 113.

In the wire-laying path 113, the resin part 130 after curing of the thermosetting resin is formed in a manner to surround the conducting wire 120.

Next, they are assembled into the scanning magnet 200 (FIG. 1) as step S08. More specifically, the two bobbins 110 are integrated together to face each other on the outside in the radial direction of the beam duct 210 in a manner to surround the beam duct 210. Note that to maintain the relative positional relation between the beam duct 210 and the bobbins 110, a not-illustrated spacer or the like may be provided.

Figure 20:
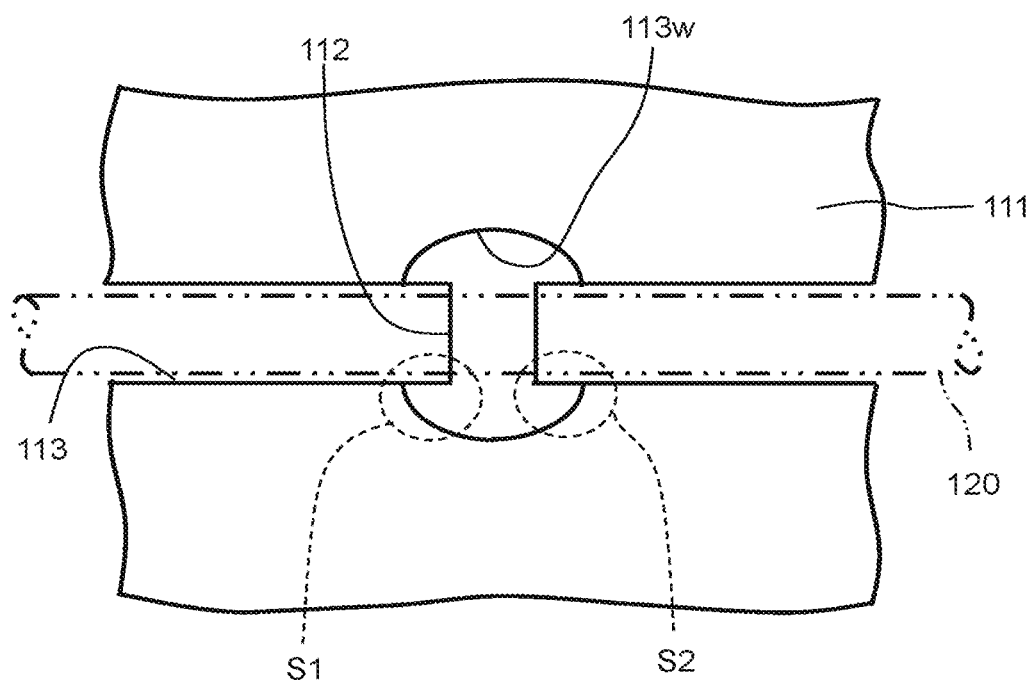
FIG. 20 is a partial plan view illustrating a wire-laying path including a widened part formed at a main body of a scanning coil according to a second embodiment.

As explained above, the conducting wire can be placed with high accuracy by this embodiment Second Embodiment FIG. 20 is a partial plan view illustrating a wire-laying path 113 including a widened part 113w formed at the main body 111 of the scanning coil according to a second embodiment.

This second embodiment is a modification of the first embodiment, in which the widened part 113w is formed at a part of the wire-laying path 113. The second embodiment is the same as the first embodiment in the other points.

The widened part 113w is formed at a position where the holding part is placed at the main body 111. At the widened part 113w, the width of the wire-laying path 113 is increased. In other words, the widened part 113w is a cut formed in the wire-laying path 113. The planar shape of the widened part 113w is illustrated using a case of a semi-elliptical shape as an example in FIG. 20 and FIG. 21, but is not limited to this. The shape may be, for example, a rectangular shape or a polygonal shape. Besides, the holding part 112 is illustrated in an example where its plane is placed at a part of the widened part 113w as illustrated in FIG. 20, FIG. 21, but may have a shape widened to the entire width in the longitudinal direction of the widened part 113w.

Figure 21:
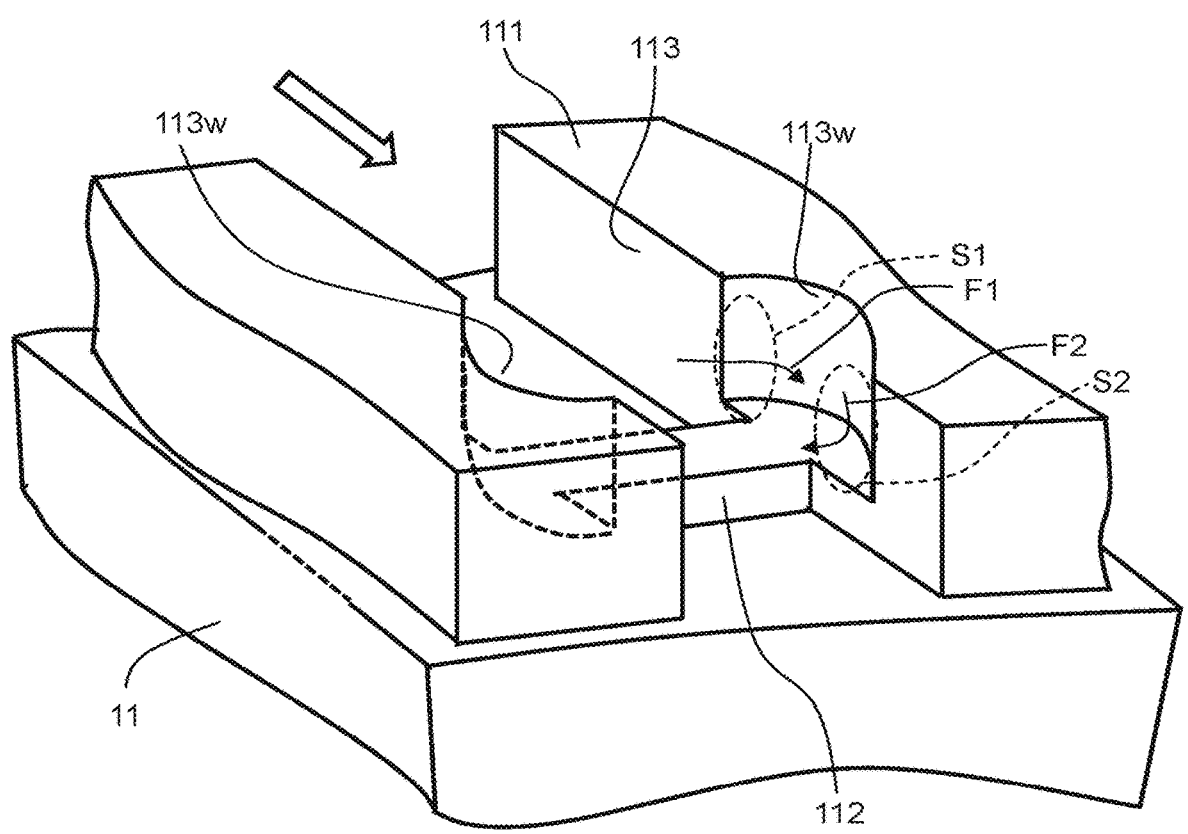
FIG. 21 is a partial perspective view illustrating the periphery of the widened part at the resin injection in the method for manufacturing the scanning coil according to the second embodiment.

FIG. 21 is a partial perspective view illustrating the periphery of the widened part 113w at the resin injection in the method for manufacturing the scanning coil according to the second embodiment. Note that the illustration of the conducting wire 120 and the outer cylinder 12 is omitted. In FIG. 21, a direction of the flow of the resin is illustrated by an outline arrow.

Owing to the existence of the widened part 113w, a space in the widened part 113w communicates with the path on the upstream side via an opening S1. Further, the space in the widened part 113w communicates with the path on the downstream side via an opening S2. In other words, the path on the upstream side and the path on the downstream side communicate with each other from the opening S1 through the widened part 113w and from the widened part 113w through the opening S2, so that the resin flows from the upstream side to the downstream side as illustrated by an arrow F1 and an arrow F2 in FIG. 21.

The above configuration ensures reliable filling with the resin by injection.

Other Embodiments

While certain embodiments of the present invention have been described, these embodiments have been presented by way of example only, and are not intended to limit the scope of the inventions. For example, the embodiments have been explained using the case where two halved bobbins are integrated together to assemble the scanning coil, but the present invention is not limited to this. For example, when integrally forming the bobbins as the scanning magnet including the beam ducts besides the beam duct at the connection destination, the bobbins not in the halved shape but an integrated shape may be produced from the beginning.

Besides, the case where the resin injecting assembly 10 is constructed and the resin is injected thereinto has been explained as an example in the embodiments, but the present invention is not limited to this. For example, a method of installing and temporarily fixing the conducting wire 120 in the wire-laying path 113 and then applying the resin using a brush or the like may be used.

The characteristics of these embodiments may be combined. The embodiments described herein may be embodied in a variety of other forms, and furthermore, various omissions, substitutions and changes may be made without departing from the spirit of the inventions. The embodiments and their modifications would fall within the scope and spirit of the inventions and would fall within the inventions as set forth in claims and their equivalents.

What is claimed is:

1. A scanning coil comprising:
a bobbin including
a main body having a truncated conical cylindrical outer shape in an integrated or assembled state and made of an electrically insulating material,
a wire-laying path formed in the main body, the wire-laying path penetrating the main body from the outside to the inside of the main body to cut thereof,
the wire-laying path having a plurality of long-side parts formed in the longitudinal direction, a plurality of small-diameter parts, and a plurality of large-diameter parts,
each of the long-side parts, the small-diameter parts, and the large-diameter parts formed in the main body reaching the inside surface from the outside surface of the main body,
the plurality of long-side parts individually extending in the longitudinal direction with circumferential intervals therebetween to connect the small-diameter parts and the large-diameter parts to form the wire-laying path, and
a plurality of holding parts formed along the wire-laying path on an inner peripheral surface side of the main body with axial intervals therebetween to bridge across the wire-laying path for maintaining whole shape of the cut main body;
a conducting wire installed along within the wire-laying path of the bobbin, the conducting wire not projecting to an interior side of the main body by the plurality of holding parts; and
a resin part filled in the wire-laying path impregnated between the bobbin and the conducting wire, the resin part surrounding the conducting wire for fixing the conducting wire within the wire-laying path.

2. The scanning coil according to claim 1, wherein
an occupancy rate of the conducting wire in the wire-laying path is 50% to 95%.

3. The scanning coil according to claim 1, wherein
the bobbin is a fiber reinforced plastic material.

4. The scanning coil according to claim 1, wherein
the bobbin forms a rotation body by integrating two bobbins together to face each other.

5. The scanning coil according to claim 1, wherein
the resin uses an anhydride-curing epoxy resin.

6. A scanning magnet comprising:
a beam duct; and
the scanning coil according to claim 1 arranged on an outside in a radial direction of the beam duct to surround the outside in the radial direction of the beam duct.

* * * * *